(12) United States Patent
Tachibana (10) Patent No.: US 7,393,429 B2
(45) Date of Patent: Jul. 1, 2008

(54) DISPOSABLE WEARING ARTICLE

(75) Inventor: Ikuo Tachibana, Settsu (JP)

(73) Assignee: Zuiko Corporation (JP)

( * ) Notice: Subject to any disclaimer, the term of this patent is extended or adjusted under 35 U.S.C. 154(b) by 482 days.

(21) Appl. No.: 10/530,259

(22) PCT Filed: Oct. 17, 2003

(86) PCT No.: PCT/JP03/13284

§ 371 (c)(1),
(2), (4) Date: Apr. 5, 2005

(87) PCT Pub. No.: WO2004/037146

PCT Pub. Date: May 6, 2004

(65) Prior Publication Data

US 2006/0052763 A1     Mar. 9, 2006

(30) Foreign Application Priority Data

Oct. 24, 2002 (JP) ............................. 2002-309306
May 28, 2003 (JP) ............................. 2003-150101

(51) Int. Cl.
*B32B 37/00* (2006.01)
*B32B 38/04* (2006.01)
*B29C 65/00* (2006.01)
*A61F 13/15* (2006.01)

(52) U.S. Cl. ...................... 156/256; 156/324; 604/395

(58) Field of Classification Search ................... 156/64, 156/250, 256, 324; 604/395

See application file for complete search history.

(56) References Cited

U.S. PATENT DOCUMENTS 5,766,389 A * 6/1998 Brandon et al. ............... 156/64
6,328,725 B2 * 12/2001 Fernfors ...................... 604/391
6,645,190 B1 * 11/2003 Olson et al. .................. 604/389
6,682,626 B2 * 1/2004 Mlinar et al. ................ 156/252

(Continued)

FOREIGN PATENT DOCUMENTS

JP        1-141711      6/1989

(Continued)

*Primary Examiner*—Melvin C. Mayes
*Assistant Examiner*—Patrick G Rodgers
(74) *Attorney, Agent, or Firm*—Gerald E. Hespos; Anthony J. Casella (57) ABSTRACT

Disclosed is a disposable wearing article, which includes a front stretchable multilayer member defining an abdominal-side front zone, a rear stretchable multilayer member defining a dorsal-side rear zone, and an absorbent body disposed to bridge between the front stretchable multilayer member and the rear stretchable multilayer member, wherein the front stretchable multilayer member and the rear stretchable multilayer member are joined together to form a waist opening. The disposable wearing article comprises at least one cutting line formed in either one of the front stretchable multilayer member and the rear stretchable multilayer member each having a first end defining the waist opening and a second end opposed to the first end, to extend between the first and second ends, and a fastening member detachably engaging between the absorbent body and the stretchable multilayer member formed with the cutting line. In this disposable wearing article, the cutting line is formed to pass through a superimposed portion of the absorbent body and the stretchable multilayer member formed with the cutting line. The fastening member is adapted to allow the disposable wearing article in the state after the stretchable multilayer member formed with the cutting line is cut open to be reconstructed and used in a pant-like configuration.

4 Claims, 11 Drawing Sheets

U.S. PATENT DOCUMENTS

| | | | |
|---|---|---|---|
| 6,827,804 B2 * | 12/2004 | Otsubo et al. | 156/161 |
| 6,979,380 B2 * | 12/2005 | Thorson et al. | 156/259 |
| 7,156,939 B2 * | 1/2007 | Vogt et al. | 156/160 |
| 7,220,335 B2 * | 5/2007 | Van Gompel et al. | 156/259 |
| 2001/0042584 A1 * | 11/2001 | Karami et al. | 156/66 |

FOREIGN PATENT DOCUMENTS

| | | | |
|---|---|---|---|
| JP | 4-144558 | | 5/1992 |
| JP | 5-317356 | * | 3/1993 |
| JP | 5-317356 | | 12/1993 |
| JP | 9-56746 | | 3/1997 |
| JP | 029389 A | * | 2/2001 |
| WO | WO 01/13848 | | 3/2001 |
| WO | WO 01/13848 A1 | * | 3/2001 |

* cited by examiner

DISPOSABLE WEARING ARTICLE

TECHNICAL FIELD

The present invention relates to a disposable wearing article.

BACKGROUND ART

Heretofore, in connection with disposable wearing articles, such as disposable pants, there has been proposed one type comprising a leg opening formed in a crotch zone located between an abdominal-side front zone and a dorsal-side rear zone, and an absorbent body disposed on a skin-side surface of the crotch zone, wherein two pairs of lateral edges of the abdominal-side front zone and the dorsal-side rear zone are fusion-bonded and joined together (so-called "side-sealed") (see, for example, Japanese Patent Laid-Open Publication No. 09-56746).

There has also been proposed a disposable diaper comprising a first mechanical fastener (fastening member) attached to each of opposite lateral edges of either one of an abdominal-side front zone and a dorsal-side rear zone of a cover sheet, and a second mechanical fastener attached to each of opposite lateral edges of a remaining one of the abdominal-side front zone and the dorsal-side rear zone, wherein the first mechanical fastener is adapted to be detachably engageable with the second mechanical fastener.

The disposable pant designed to side-seal an abdominal-side front zone and a dorsal-side rear zone of a cover sheet, as disclosed in the above Patent Publication 1, is excellent in peel strength. On the other hand, it involves a problem that, if a wearer tears a side portion of the pant and opens the abdominal-side front zone to discharge his/her urine or the like in an urgent situation, he/she has to change the pant to new one on the scene because the side portion cannot be re-attached.

While the disposable wearing pant designed to engage between an abdominal-side front zone and a dorsal-side rear zone of a cover sheet by means of a mechanical fastener allow an engaging/disengaging operation to be repeatedly performed, it involves a problem about poor engagement strength which is liable to cause loose in engagement and sagging of the pant during long-term use.

In view of the above problems, it is therefore an object of the present invention to provide a disposable wearing article adapted to be usable in a pant-like configuration in a normal situation, and to allow a side portion or the like, which is torn in an urgent situation, to be temporarily re-engaged using a fastening member so as to maintain a pant-like configuration until it is changed to a new wearing article.

DISCLOSURE OF INVENTION

The present invention provides a disposable wearing article including a front stretchable multilayer member defining an abdominal-side front zone, a rear stretchable multilayer member defining a dorsal-side rear zone, and an absorbent body disposed to bridge between the front stretchable multilayer member and the rear stretchable multilayer member, wherein the front stretchable multilayer member and the rear stretchable multilayer member are joined together to form a waist opening. The disposable wearing article comprises at least one cutting line formed in either one of the front stretchable multilayer member and the rear stretchable multilayer member each having a first end defining the waist opening and a second end opposed to the first end, to extend between the first and second ends, and a fastening member detachably engaging between the absorbent body and the stretchable multilayer member formed with the cutting line. In this disposable wearing article, the cutting line is formed to pass through a superimposed portion of the absorbent body and the stretchable multilayer member formed with the cutting line.

Preferably, the fastening member is adapted to allow the disposable wearing article in the state after the stretchable multilayer member formed with the cutting line is cut open to be reconstructed and used in a pant-like configuration.

According to the present invention, a side-sealed structure for fusion-bonding two pairs of lateral edges of the abdominal-side front zone and the dorsal-side rear zone in a peelable manner can be used to provide excellent peel strength in side portions of the disposable wearing article. Thus, in normal use, the side portions never get loose even if the disposable wearing article is used in a pant-like configuration for a long period of time.

Further, the structure designed to detachably engage between the abdominal-side front zone and the dorsal-side rear zone by means of the fastening member is used in combination. Thus, after the side-sealed portion is peeled and separated in an urgent situation, the separated portions can be temporarily re-engaged using the fastening member to maintain a pant-like configuration until the wearing article is changed to new one.

This makes it possible to make full use of a costly disposable wearing article effectively.

BRIEF DESCRIPTION OF DRAWINGS

FIGS. 2A and 2B show the disposable pant in FIG. 1, wherein

FIGS. 6A and 6B show the disposable pant in FIG. 5, wherein

FIGS. 7A to 7C show a disposable pant having a single cutting line, according to a third embodiment of the present invention, wherein

FIGS. 9A to C show a disposable pant having two cutting lines, wherein

BEST MODE FOR CARRYING OUT THE INVENTION

With reference to the drawings, an embodiment of the present invention will now be described in detail.

As shown in FIGS. 1, 2A, 2B and 3A, a disposable pant 15A, which is a disposable wearing article according to a first embodiment of the present invention, fundamentally comprises: an absorbent body 1 including a pair of backsheets 2 (A, B), an absorbent core 3 and a topsheet 4; a pair of right and left risable flaps 5; and a rear stretchable sheet 6 for a dorsal-side rear zone. In this fundamental structure, the backsheet 2A may be omitted therefrom, and a leg elastic member 9 may be additionally attached in its stretched state between the backsheet 2B and the topsheet 4, or between the backsheet 2B and each of the risable flaps 5, along each of a pair of leg openings S.

Figure 1:
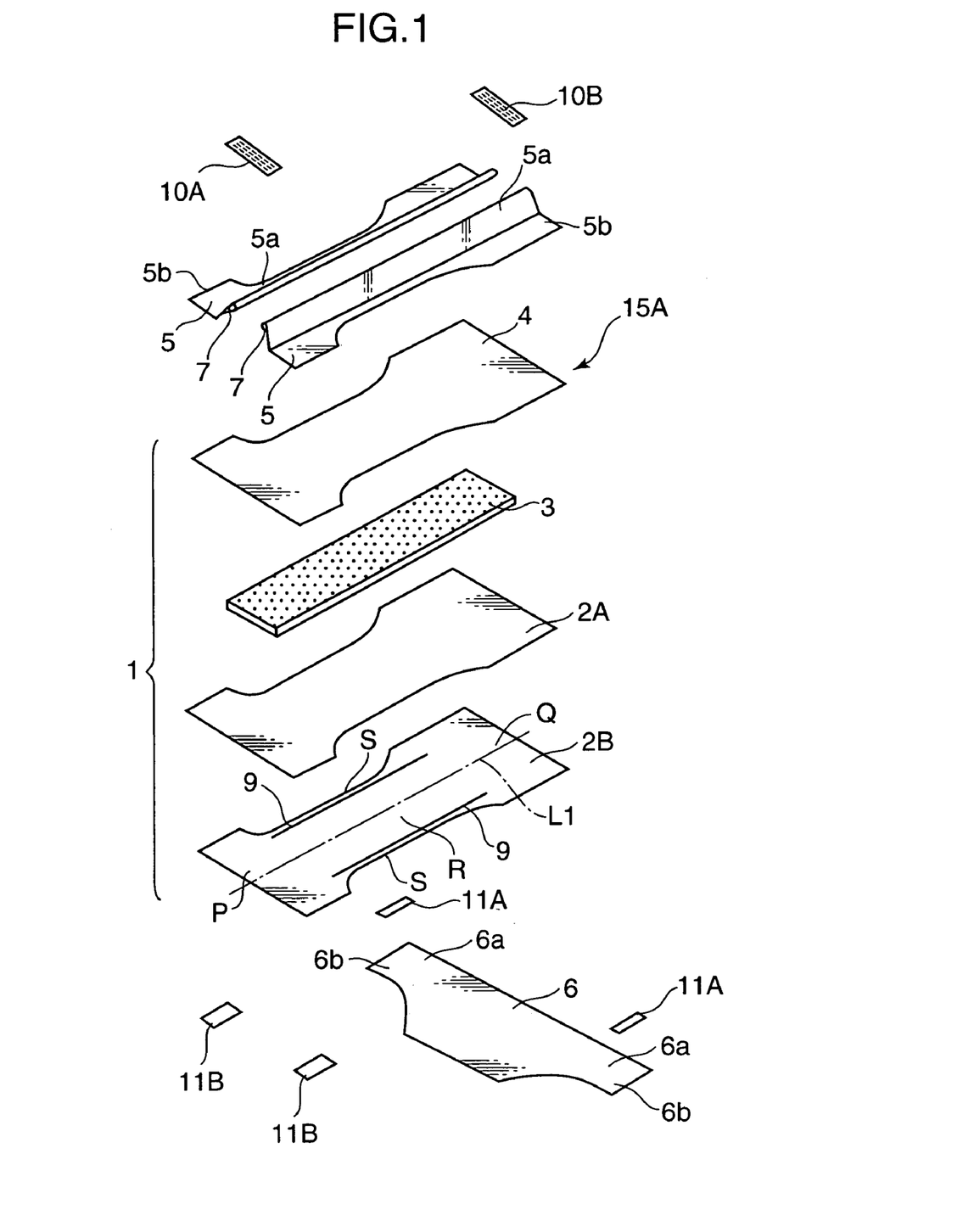
FIG. 1 is an explored perspective view of a disposable pant according to a first embodiment of the present invention.
Figure 2A:
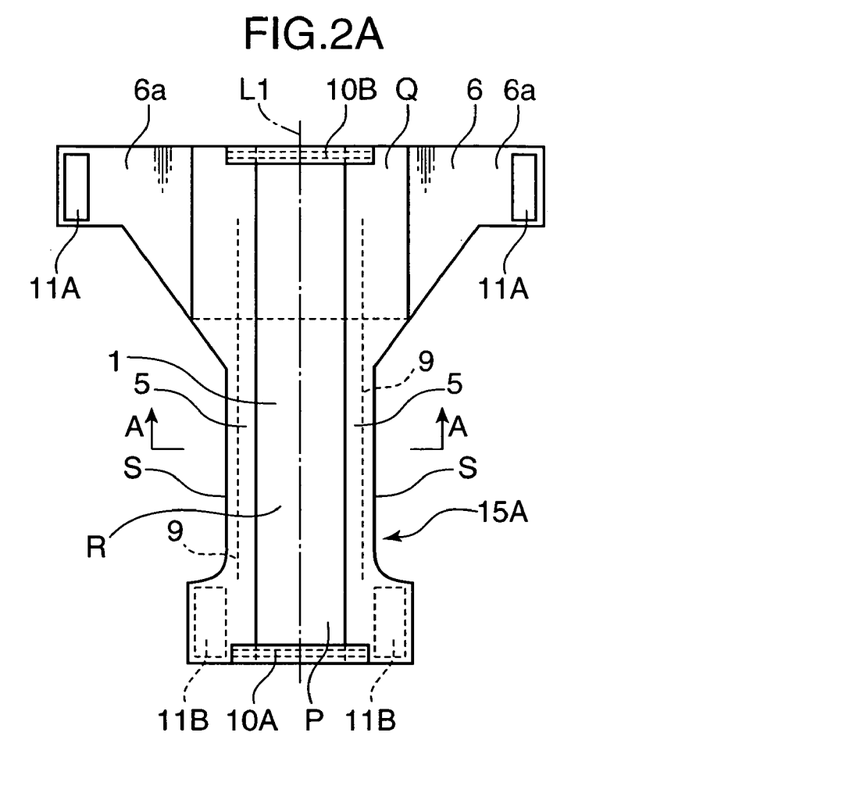
FIG. 2A is a developed front view thereof.
Figure 3A:
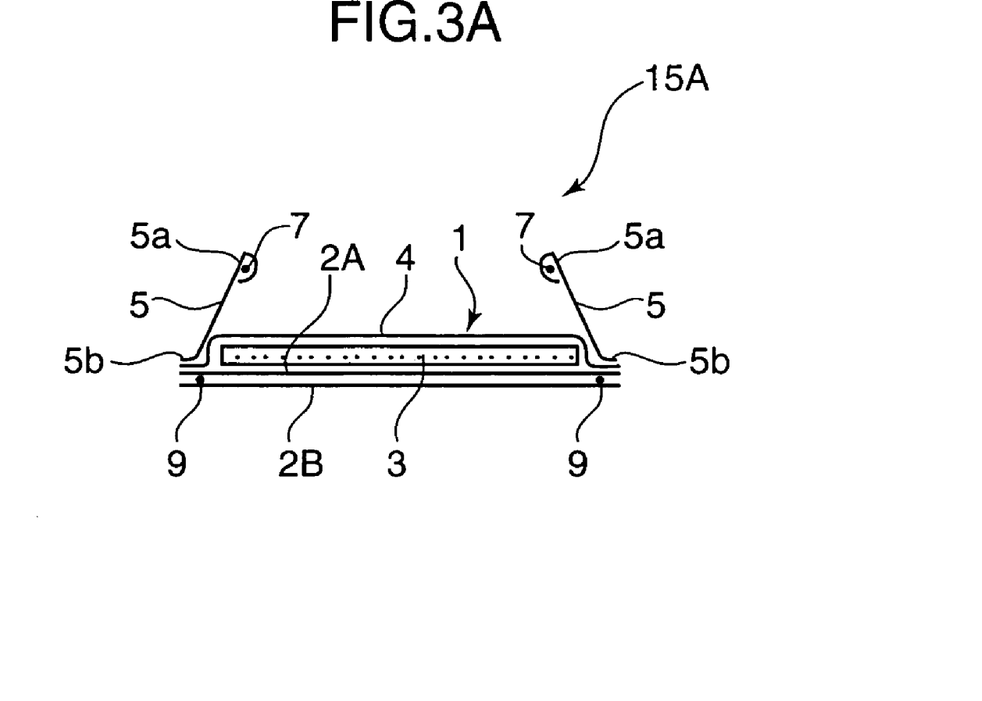
FIG. 3A is a sectional view taken along the line A-A in FIG. 2A.

At least one of the backsheets 2 (A, B) is made of a liquid-impervious material. A synthetic resin film or a water-shedding nonwoven may be suitably used as the liquid-impervious material, and a nonwoven may be suitably used as a liquid-pervious material therefor. The leg elastic member 9 is attached in its stretched state between the two backsheets 2 (A, B) to be bonded to one another in a superimposed manner, along each of lateral edges of the backsheets 2 (A, B).

The absorbent core 3 is made of a natural pulp fiber, a synthetic resin fiber, a superabsorbent resin material or the like.

The topsheet 4 is made of a liquid-pervious nonwoven.

The pair of right and left risable flaps 5 are made of a synthetic resin nonwoven having water-shedding properties or waterproofing properties. Each of the risable flaps 5 includes a flap elastic member 7 bonded in its stretched state to a free end 5a thereof to extend the longitudinal direction of the absorbent body 1.

Each of the elastic members 7, 9 may be formed of thread-like natural rubber, thread-like natural synthetic rubber or polyurethane-based elastic yarn, and may be provided in a number of one or more. Alternatively, each of the elastic members 7, 9 may be formed of a polyurethane-based, polyolefin-based or polystyrene-based elastic film.

The absorbent body 1 is formed by bonding the absorbent core 3 onto the upper backsheet 2(A), and bonding the topsheet 4 onto the upper backsheet 2(A) in such a manner as to wrap around the absorbent core 3. Then, the anchor end 5b of each of the risable flaps 5 is bonded to a corresponding one of opposite lateral edges of the obtained absorbent body 1.

This absorbent body 1 has an abdominal-side front zone P located at one of longitudinal ends thereof, a dorsal-side rear zone Q located at the other end, and a crotch zone R between the abdominal-side front zone P and the dorsal-side rear zone Q. The crotch zone R is formed with the leg openings S on opposite sides of an axis L1 extending in the longitudinal direction.

A waist elastic sheet 10A having a waist elastic member attached thereto is bonded to the front end of the abdominal-side front zone P of the absorbent body 1, and a waist elastic sheet 10B having a waist elastic member attached thereto is bonded to the rear end of the dorsal-side rear zone Q. These elastic sheets 10A, 10B are bonded, respectively, to the abdominal-side front zone P and the dorsal-side rear zone Q, in such a manner as to sandwich the front and rear ends of the risable flaps 5 therebetween. The bonding of the elastic sheets 10A, 10B is not limited to the above example where they are bonded, respectively, to the abdominal-side front zone P and the dorsal-side rear zone Q, in such a manner as to sandwich the front and rear ends of the risable flaps 5 therebetween. Further, the waist elastic sheet 10B may be omitted, and the rear stretchable sheet 6 may be bent to wrap the rear end of the risable flaps 5, and bonded thereto.

The stretchable sheet 6 is bonded on a back surface of the backsheet 2(B) in the dorsal-side rear zone Q of the absorbent body 1 to form a pair of laterally-extending side areas 6a on the side of opposite lateral edges of the stretchable sheet 6. A hook element 11A of a mechanical fastener 11 is bonded onto an inner surface of a free edge in each of the side areas 6a, and a loop element 11B of the mechanical fastener 11 is bonded onto each of opposite lateral edges of an outer surface of the backsheet 2(B) in the abdominal-side front zone P of the absorbent body 1.

When the loop element and the hook element make a pair, the reference numerals 11A and 11B may indicate the loop element and the hook element, respectively. Further, in the case where the hook element is disposed on the inner surface of the free edge in each of the side areas 6a, and the loop element is disposed on each of opposite lateral edges of the outer surface of the backsheet 2(B), if the outer surface of the backsheet 2(B) is made of a material detachably engageable with the hook element (e.g. air-through bonded nonwoven), it can be used as substitute for the loop element 11B.

As used in the specification, the term "mechanical fastener (11)" means a fastener, so-called "surface fastener", which comprises a pair of a hook element (11A) and a loop element (11B), wherein the hook element (11A) and the loop element (11B) can be engaged together with an adequate disengagement resistance by strongly pressing them to one another, and the engagement between the hook element (11A) and the loop element (11B) can be released by strongly peeling them from one another manually.

Figure 4A:
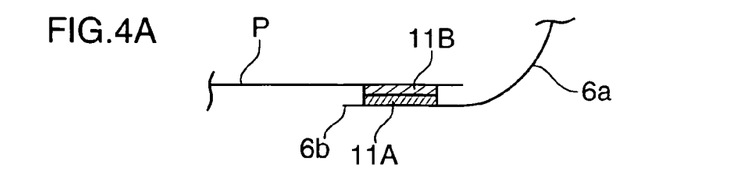
FIG. 4A is an enlarged top plan view of an engaged portion based on a mechanical fastener.

As shown in FIG. 4A, the hook element 11A of the mechanical fastener 11 attached on each of the side areas 6a of the stretchable sheet 11 can be engaged with a corresponding one of the loop elements 11B attached on the backsheet 2(B) in the abdominal-side front zone P of the absorbent body 1 so as to establish the engagement between the abdominal-side front zone P and the dorsal-side rear zone Q through the mechanical fastener 11.

Fundamentally, each of the side areas 6a of the stretchable sheet 11 has a side-sealed structure where it is fusion-bonded in a peelable manner to a corresponding one of opposite lateral edges of the outer surface of the backsheet 2(B) in the abdominal-side front zone P of the absorbent body 1.

Figure 4B:
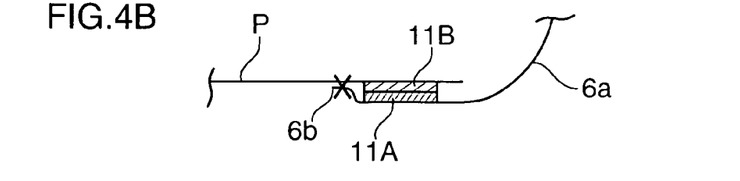
FIGS. 4B to 4H are enlarged top plan views of various side-sealed portions based on fusion bonding.

Specifically, as shown in FIG. 4B, the hook element 11A of the side area 6a is engaged with the loop elopement 11B in the abdominal-side front zone P, and then the edge 6b of the side area 6a is fusion-bonded (see the mark "X") to the abdominal-side front zone P to form the side-sealed structure.

Figure 4C:
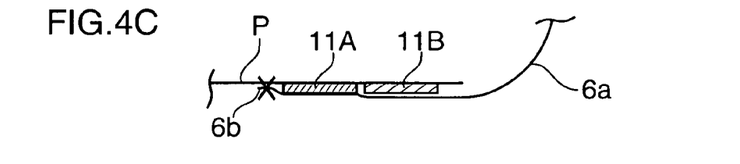
Figure 4D:
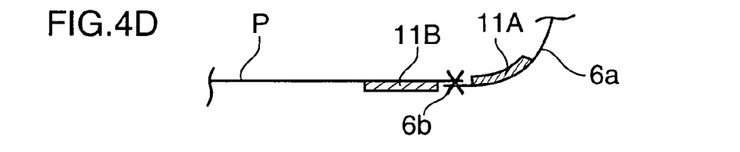

This side-sealed structure may be formed by placing the hook element 11A of the side area 6a at an inward position relative to the loop element 11B of the abdominal-side front zone P in a non-engaged manner, and then fusion-bonding (see the mark "X") the edge 6b of the side area 6a to the abdominal-side front zone P, as shown in FIG. 4C, or by placing the hook element 11A of the side area 6a at an outward position relative to the loop element 11B of the abdominal-side front zone P in a non-engaged manner, and then fusion-bonding (see the mark "X") the edge 6b of the side area 6a to the abdominal-side front zone P, as shown in FIG. 4D.

Figure 4E:
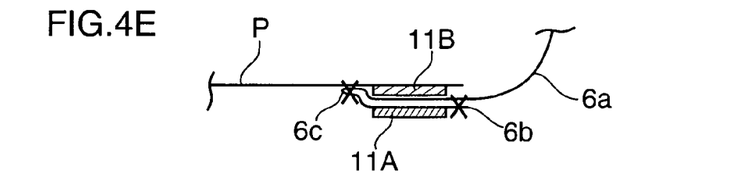
Figure 4F:
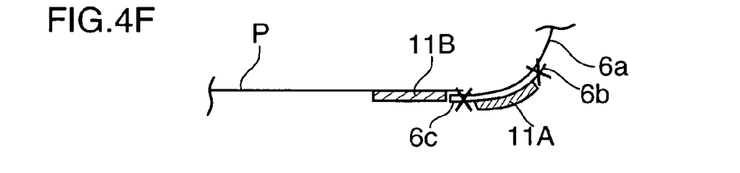

Alternatively, the side-sealed structure may be formed by outwardly folding back the hook element 11A of the side area 6a to superimpose the hook element 11A on the loop element 11B of the abdominal-side front zone P, then fusion-bonding (see the mark "X") the folded portion 6c of the side area 6a to the abdominal-side front zone P, and additionally fusion-bonding (see the mark "X") the edge 6b of the side area 6a to the side area 6a, as shown in FIG. 4E, or by outwardly folding back the hook element 11A of the side area 6a to place the hook element 11A at an outward position relative to the loop element 11B of the abdominal-side front zone P, then fusion-bonding (see the mark "X") the folded portion 6c of the side area 6a to the abdominal-side front zone P, and additionally fusion-bonding (see the mark "X") the edge 6b of the side area 6a to the side area 6a, as shown in FIG. 4F.

Figure 4G:
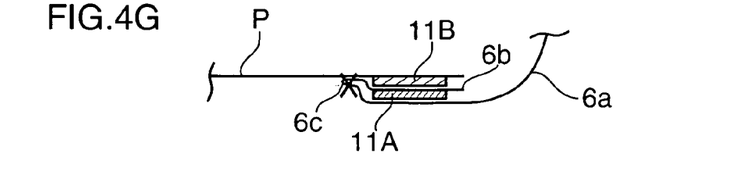
Figure 4H:
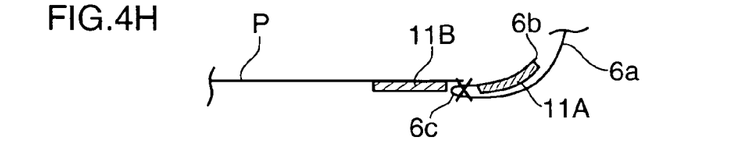

Alternatively, the side-sealed structure may be formed by inwardly folding back the hook element 11A of the side area 6a to superimpose the hook element 11A on the loop element 11B of the abdominal-side front zone P, and then fusion-bonding (see the mark "X") the folded portion 6c of the side area 6a to the abdominal-side front zone P, as shown in FIG. 4G, or by inwardly folding back the hook element 11A of the side area 6a to place the hook element 11A at an outward position relative to the loop element 11B of the abdominal-side front zone P, and then fusion-bonding (see the mark "X") the folded portion 6c of the side area 6a to the abdominal-side front zone P, as shown in FIG. 4H.

FIGS. 4B to 4H show just some examples of the side-sealed structures, and any other suitable side-sealed structure formed by fusion-bonding two pairs of lateral edges of the abdominal-side front zone P and the dorsal-side rear zone Q in a peelable manner may be used.

Figure 2B:
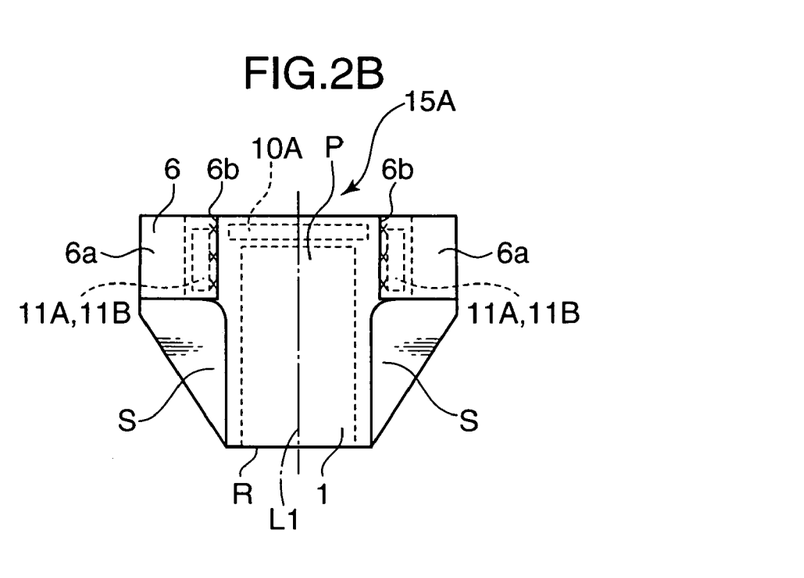
FIG. 2B is a front view thereof during use.

The above disposable pant 15A according to the first embodiment has the side-sealed structure formed by fusion-bonding the lateral edges of the abdominal-side front zone P and the corresponding lateral edges of the side areas 6a of the stretchable sheet 6 in the dorsal-side rear zone Q, in a peelable manner. This side-sealed structure has excellent peel strength. Thus, in normal use, the side-sealed portions never get loose even if the disposable pant 15A is used for a long period of time, and thereby can suppress sagging of the disposable pant 15A.

The above disposable pant 15A also has the structure designed to engage between the abdominal-side front zone P and the side areas 6a of the stretchable sheet 6 in the dorsal-side rear zone Q by means of the mechanical fastener 11. Thus, when the side-sealed portion is peeled and separated in an urgent situation, the separated portions can be temporarily re-engaged using the mechanical faster 11 until the disposable pant 15A is changed to new one, so as to eliminate the problem that the disposable pant 15A has to be changed to new one on the scene.

This makes it possible to make full use of the costly disposable pant 15A effectively.

Further, in this embodiment, the hook elements 11A of the mechanical fastener 11 are attached to the stretchable sheet 6 in the dorsal-side rear zone Q. This stretchable sheet 6 can provide enhanced fit of the disposable pant 15A to the periphery of the waist of a wearer, and thereby achieve improved wearing feel while preventing sagging.

While the disposable pant 15A according to the first embodiment is a type in which the abdominal-side front zone P and the dorsal-side rear zone Q are formed in the absorbent body 1, the abdominal-side front zone P and the dorsal-side rear zone Q may be formed in an cover sheet 12, as shown in a disposable pant 15B according to a second embodiment of the present invention illustrated in FIGS. 5, 6A, 6B and 3B.

Figure 5:
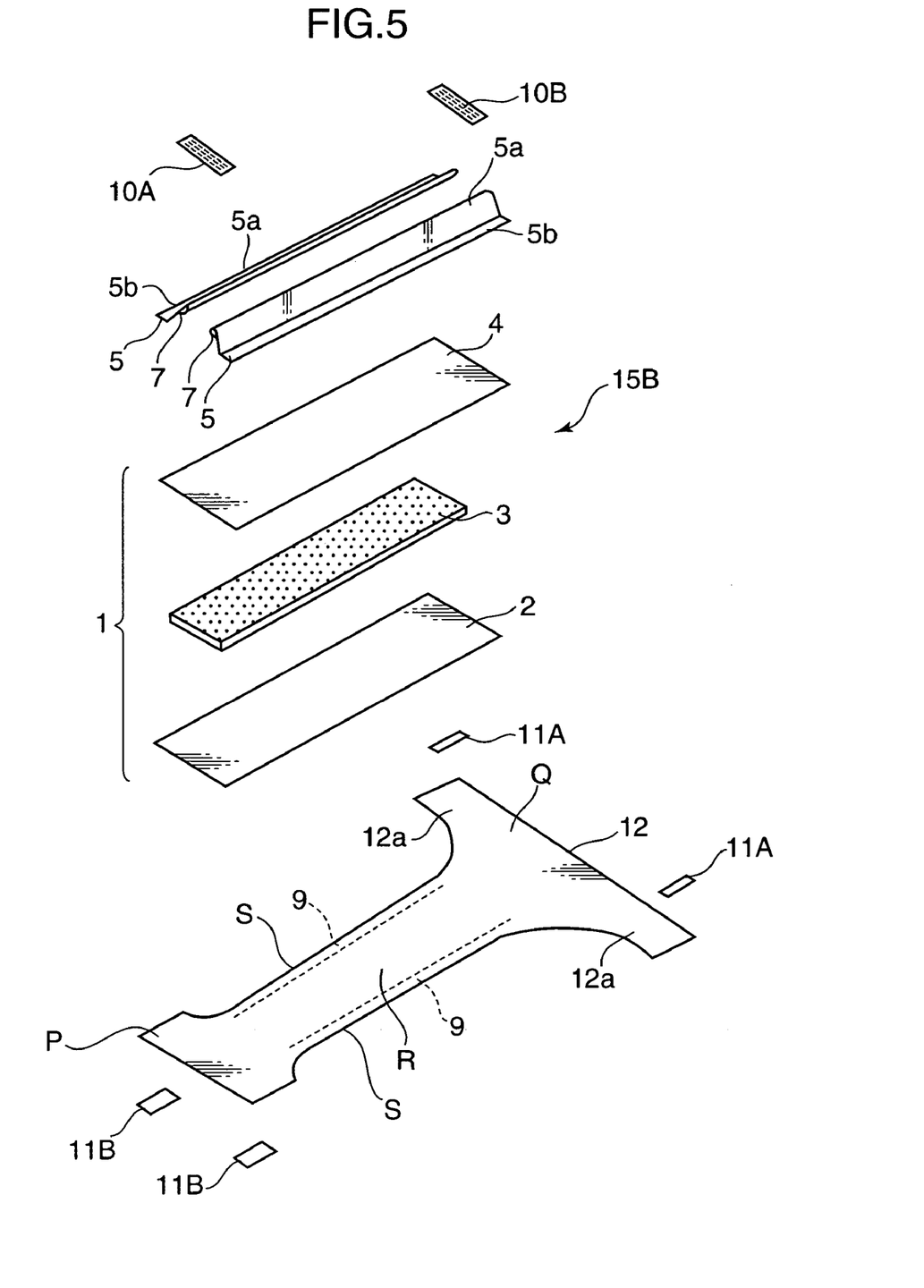
FIG. 5 is an explored perspective view of a disposable pant according to a second embodiment of the present invention.

Specifically, the disposable pant 15B according to the second embodiment fundamentally comprises: a cover sheet 12; an absorbent body 1 including a single backsheet 2, an absorbent core 3, and a topsheet 4; and a pair of right and left risable flaps 5.

The backsheet 2 is made of a liquid-impervious material, and the absorbent core 3 is made of a natural pulp fiber, a synthetic resin fiber, a superabsorbent resin material or the like. The topsheet 4 is made of a liquid-pervious nonwoven.

The pair of right and left risable flaps 5 are made of a synthetic resin nonwoven having water-shedding properties or waterproofing properties. Each of the risable flaps 5 includes a flap elastic member 7 bonded in its stretched state to a free end 5a thereof to extend the longitudinal direction of the absorbent body 1.

The absorbent body 1 is formed by bonding the absorbent core 3 onto the backsheet 2, and bonding the topsheet 4 onto the backsheet 2 in such a manner as to wrap around the absorbent core 3. Then, the anchor end 5b of each of the risable flaps 5 is bonded to a corresponding one of opposite lateral edges of the obtained absorbent body 1.

Figure 3B:
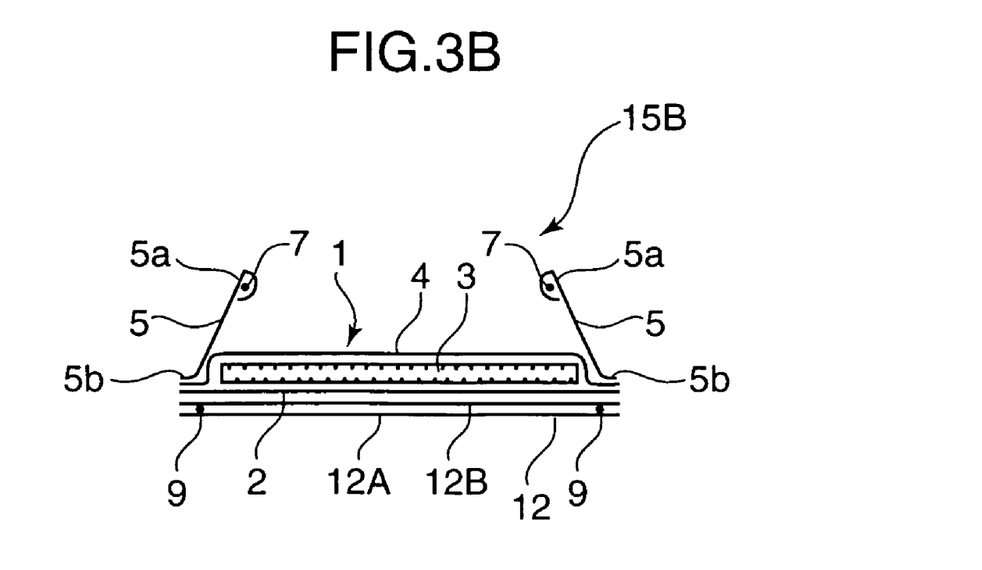
FIG. 3B is a sectional view taken along the line B-B in FIG. 6A.

As shown in FIG. 3B, the cover sheet 12 comprises two sheets consisting of an outer sheet 12A and a skin-side sheet 12B. The cover sheet 12 has a front portion defining a wide abdominal-side front zone P to be applied onto the abdominal region of a wearer, and a rear portion defining a wide dorsal-side rear zone Q to be applied onto the dorsal region of the wearer. The cover sheet 12 also has a pair of leg openings S formed along opposite lateral edges of a crotch zone R located between the abdominal-side front zone P and the dorsal-side rear zone Q. Further, a leg elastic member 9 is attached in its stretched state to each of opposite lateral edges of the outer sheet 12A and the skin-side sheet 12B which are to be bonded to one another in a superimposed manner, along each of the leg openings S. The cover sheet 12 may be composed of only the outer sheet 12A. In this case, a leg elastic member 9 may be attached in its stretched state to each of lateral edges on opposite sides of the axis L1 and between the outer sheet 12B and the topsheet 4, or between the outer sheet 12B and each of the risable flaps 5. Alternatively, a leg elastic member 9 may be attached in its stretched state to each of lateral edges on opposite sides of the axis L1 and between the backsheet 2 and the topsheet 4, or between the backsheet 2 and each of the risable flaps 5.

A waist elastic sheet 10A having a waist elastic member attached thereto is bonded to the front end of the abdominal-side front zone P of the cover sheet 12, and a waist elastic sheet 10B having a waist elastic member attached thereto is bonded to the rear end of the dorsal-side rear zone Q. These elastic sheets 10A, 10B are bonded, respectively, to the abdominal-side front zone P and the dorsal-side rear zone Q, in such a manner as to sandwich the front and rear ends of the risable flaps 5 therebetween. The bonding of the elastic sheets 10A, 10B is not limited to the above example where they are bonded, respectively, to the abdominal-side front zone P and the dorsal-side rear zone Q, in such a manner as to sandwich the front and rear ends of the risable flaps 5 therebetween.

Figure 6A:
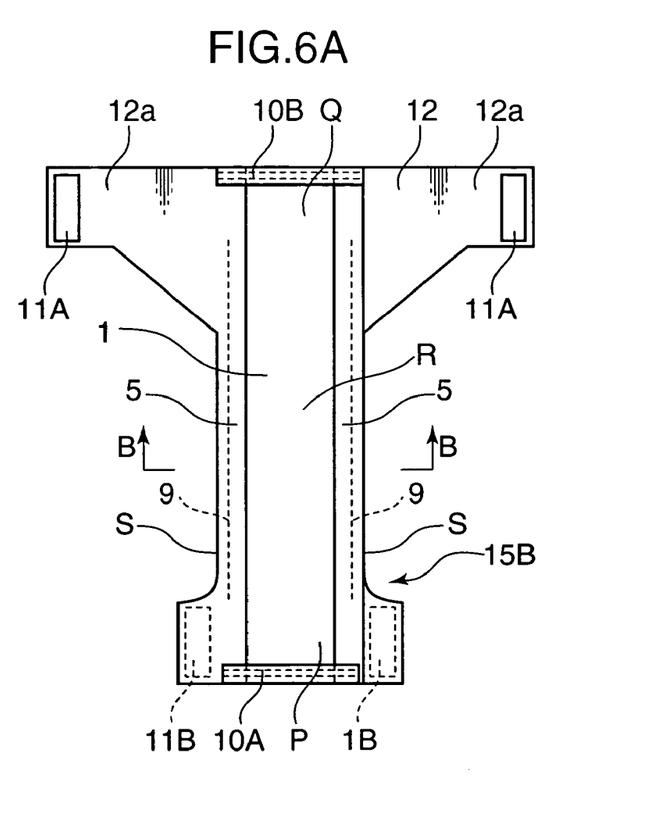
FIG. 6A is a developed front view thereof.

A hook element 11A of a mechanical fastener 11 is bonded onto an inner surface of each of the side areas 12a on opposite sides of the dorsal-side rear zone Q of the cover sheet 12, and a loop element 11B of the mechanical fastener 11 is bonded onto each of opposite lateral edges of an outer surface of the abdominal-side front zone P of the cover sheet 12.

As with the side areas 6a of the stretchable sheet 6 in the first embodiment, each of the side areas 12a of the cover sheet 12 is fundamentally fusion-bonded in a peelable manner to a corresponding one of opposite lateral edges of the outer surface of the abdominal-side front zone P of the cover sheet 12 to form a side-sealed structure which is equivalent to the side-sealed structures illustrated in FIGS. 4B to 4H.

Figure 6B:
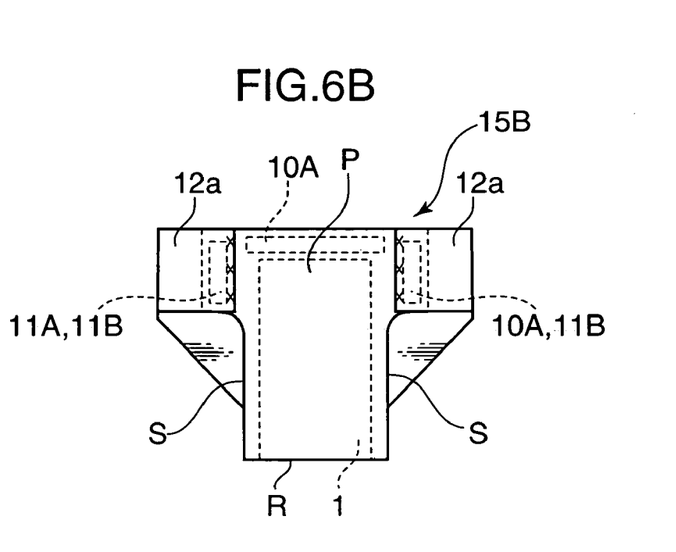
FIG. 6B is a front view thereof during use.

The above disposable pant 15B according to the second embodiment has the side-sealed structure formed by fusion-bonding the lateral edges of the abdominal-side front zone P and the corresponding lateral edges of the side areas 12a of the dorsal-side rear zone Q, in a peelable manner. This side-sealed structure has excellent peel strength. Thus, in normal use, the side-sealed portions never get loose even if the disposable pant 15B is used for a long period of time, and thereby can suppress sagging of the disposable pant 15B.

The above disposable pant 15B also has the structure designed to engage between the abdominal-side front zone P and the side areas 12a of the dorsal-side rear zone Q by means of the mechanical fastener 11. Thus, when the side-sealed portion is peeled and separated in an urgent situation, the separated portions can be temporarily re-engaged using the mechanical faster 11 until the disposable pant 15B is changed to new one, so as to eliminate the problem that the disposable pant 15B has to be changed to new one on the scene.

This makes it possible to make full use of the costly disposable pant 15B effectively.

FIGS. 7A to 10D show a disposable pant 15C according to a third embodiment of the present invention.

Figure 7A:
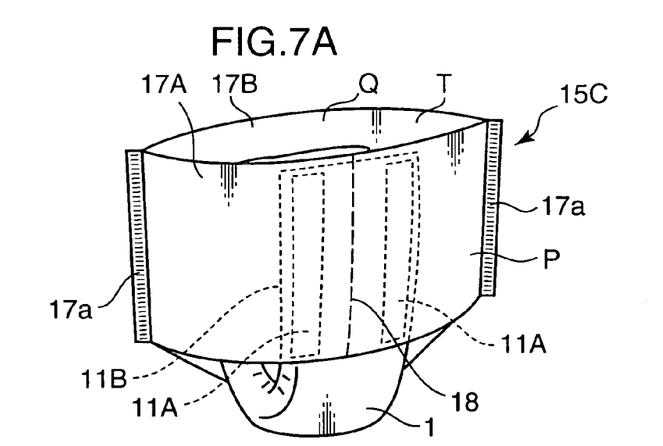
FIG. 7A is a perspective view thereof.
Figure 8A:
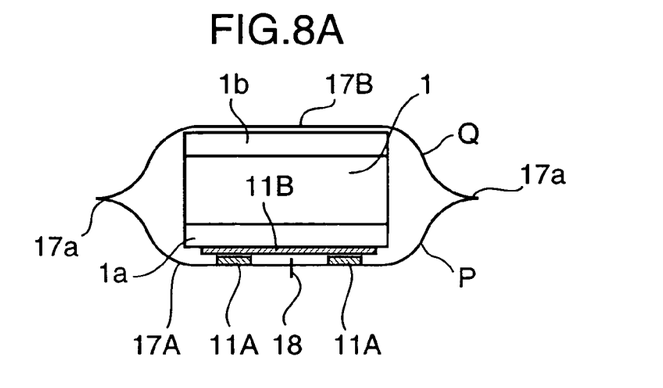
FIG. 8A is a top plan view of the disposable pant in FIG. 7A.

As shown in FIGS. 7A and 8A, this disposable pant 15C comprises a front stretchable multilayer member 17A defining an abdominal-side front zone P, and a rear stretchable multilayer member 17B defining a dorsal-side rear zone Q. Corresponding lateral edge 17a of the stretchable multilayer members 17A, 17B are fusion-bonded together (the fusion-bonded lateral edges 17a will hereinafter be referred to as "side-sealed portion 17a) to form a waist opening T. It is not essential to form the side-sealed portion 17a in a peelable manner. Instead of a fusion bonding process, the side-sealed portion 17a may be formed by any other suitable bonding process, such as an adhesive bonding process using hot melt adhesive or the like.

While a specific illustration is omitted, as with the aforementioned embodiments, an absorbent body 1 comprises a backsheet 2, an absorbent core 3, a topsheet 4, and a pair of right and left risable flap 5.

The absorbent body 1 is disposed to bridge between respective inner surfaces of the front stretchable multilayer member 17A defining the abdominal-side front zone P and the rear stretchable multilayer member 17B defining the dorsal-side rear zone Q, and an outer surface of one end (rear end) of the absorbent body 1 on the side of the dorsal-side rear zone Q is bonded onto an inner surface of the rear stretchable multilayer member 17B defining the dorsal-side rear zone Q by use of hot melt adhesive or the like.

The front stretchable multilayer member 17A is a formed with a cutting line 18 allowing the front stretchable multilayer member 17A to be manually cut in the width direction thereof. The front stretchable multilayer member 17A has a first end defining the waist opening T and a second end opposed to the first end, and the cutting line 18 is formed to extend between the first and second ends. Preferably, the cutting line 18 is formed to extend in a direction orthogonal to the first end defining the waist opening T so as to facilitate the cutting operation, and position-adjustment or alignment during an after-mentioned temporary engagement operation.

A hook element 11A of a mechanical fastener 11 is attached onto an inner surface of the front stretchable multilayer member 17A at a position located on each of outwardly right and left sides of the cutting line 18, and a loop element 11B of the mechanical fastener 11 is attached onto an outer surface of the front end 1a of the absorbent body 1. Alternatively, the hook elements 11A of a mechanical fastener 11 may be attached onto outer surface of the front end 1a of the absorbent body 1, and the loop element 11B may be attached onto the inner surface of the front stretchable multilayer member 17A. If the outer surface of the backsheet 2(B) is made of a material detachably engageable with the hook element (e.g. air-through bonded nonwoven), it can be used as substitute for the loop element 11B.

Preferably, a portion of the front stretchable multilayer member 17A corresponding to the loop element 11B is subjected to a treatment for reducing or eliminating the stretchability thereof so as to facilitate the attachment of the mechanical fastener 11 and prevent the occurrence of wrinkles in a mechanical fastener area of a finished disposable pant 15.

In the above disposable pant 15C according the third embodiment, the cutting line 18 is formed in the front stretchable multilayer member 17A defining the abdominal-side front zone P, and the absorbent body 1 is detachably engaged with the abdominal-side front zone P by means of the mechanical fastener 11. This allows the cutting line 18 to have excellent tension strength. Thus, in normal use, even if the disposable pant 15C is used in a pant-like configuration for a long period of time, the cutting line 18 will never be unexpectedly broken (or can keep the state illustrated in FIG. 7A or 8A).

Figure 7B:
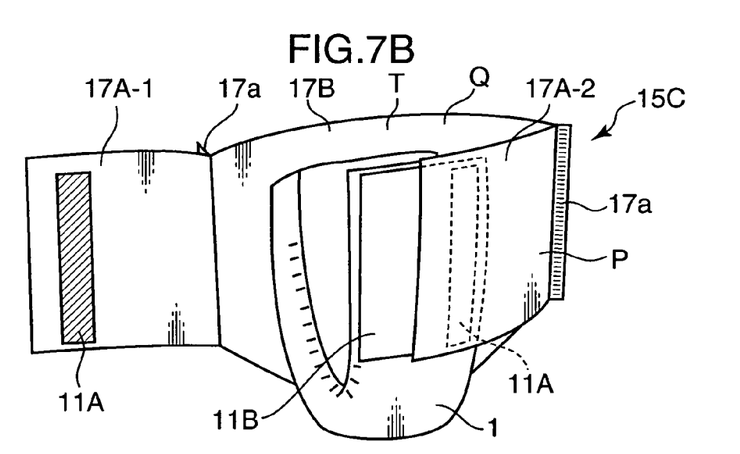
FIG. 7B is a perspective view thereof in the state after a first one of two cut segments is opened.

The disposable pant 15C also has the structure designed to engage the cut segments of the front stretchable multilayer member 17A by means of the mechanical fastener 11. Thus, after the front stretchable multilayer member 17A is cut along the cutting line 10 in an urgent situation, and one or both of first and second cut segments 17A-1, 17A-2 of the front stretchable multilayer member 17A are opened rightwardly and/or leftwardly as shown in FIG. 7B to allow a wearer to discharge his/her urine or the like in the state after the abdominal-side front zone P is opened, the cut segments 17A-1, 17A-2 can be temporarily engaged together by the mechanical fastener 11 to maintain a pant-like configuration until the disposable pant 15C is changed to new one. Preferably, the absorbent body 1 is disposed such that the terminal of the end (front end) of the absorbent body 1 on the side of the abdominal-side front zone P reaches the waist opening T, and the cutting line 18 is formed to extend within the range of the superimposed portion of the front stretchable multilayer member 17A and the absorbent body 1, wherein the mechanical fastener is attached to the entire superimposed portion. In this case, the temporary engagement strength can be desirably increased.

This makes it possible to make full use of the costly disposable pant 15C effectively.

Furthermore, the cutting line 18 may be formed as a perforated line or perforations to simplify a production process and facilitate the cutting operation.

Figure 8B:
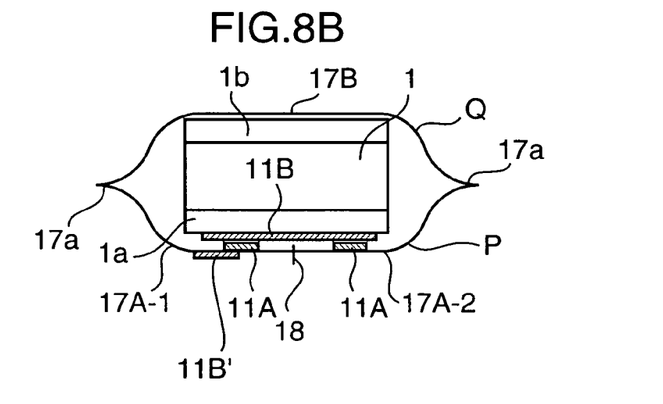
FIG. 8B is a top plan view of the disposable pant in FIG. 7A, wherein a loop element is attached to the first cut segment.

As shown in FIG. 8B, an additional loop element 11B' of the mechanical fastener 11 may be attached onto the outer surface of an area having no cutting line 18 (aforementioned first cut segment 17A-1) in the front stretchable multilayer member 17A. If the outer surface of the front stretchable multilayer member 17A is made of a material detachably engageable with the hook element (e.g. air-through bonded nonwoven), it can be used as substitute for the loop element 11B'.

Figure 7C:
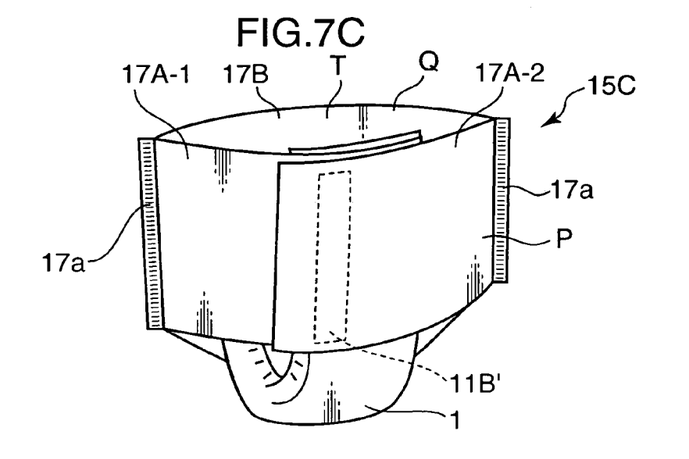
FIG. 7C is perspective view thereof in the state after a second cut segment is partly superimposed on the first cut segment.
Figure 8C:
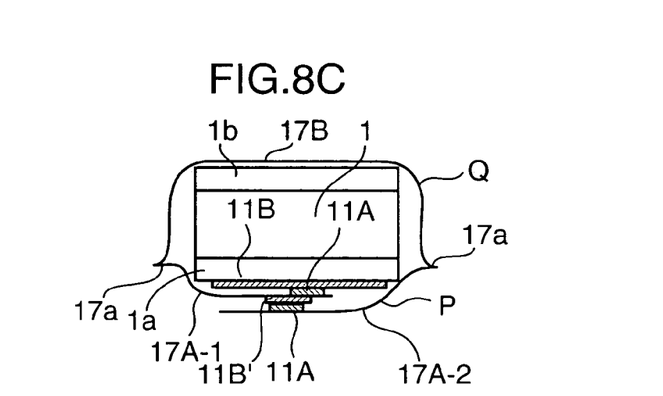
FIG. 8C is a top plan view of the disposable pant in FIG. 7C.

According to the above structure, as shown in FIGS. 7C and 8C, the first cut segment 17A-1 of the front stretchable multilayer member 17A is disposed on the inside relative to the second cut segment 17A-2, and the hook element 11A of the first cut segment 17A-1 is engaged with the loop element 11B of the absorbent body 1. Then, the second cut segment 17A-2 is superimposed on the first cut segment 17A-1 from the outside to allow the hook element 11A of the second cut segment 17A-2 to be engaged with the loop element 11B' on the outer surface of the first cut segment 17A-1.

This provides enhanced flexibility in an operation for adjusting the length around the waist, or the circumference, of the abdominal-side front zone P.

Figure 9A:
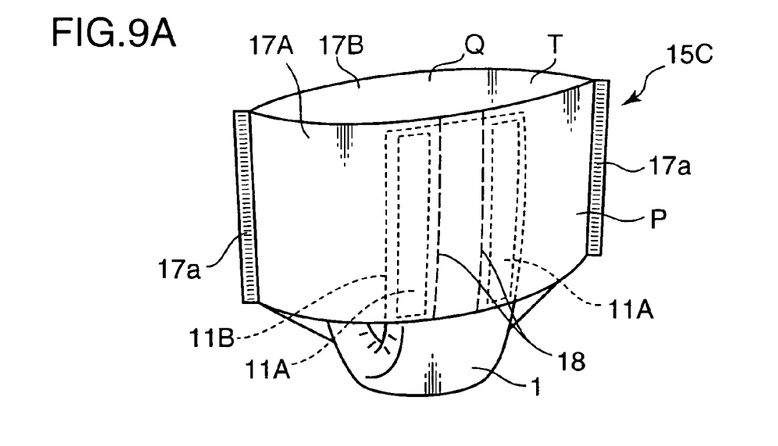
FIG. 9A is a perspective view thereof.
Figure 10A:
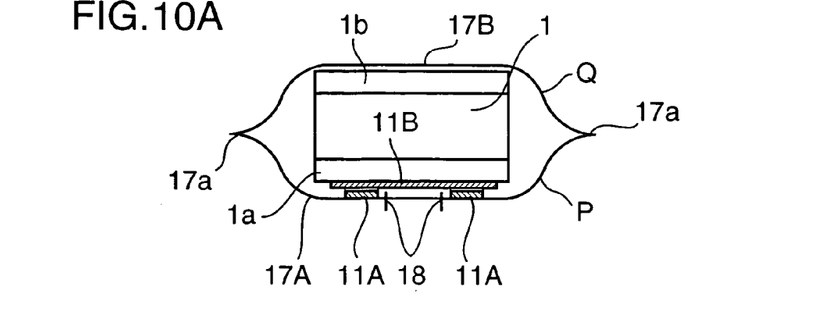
FIG. 10A is a top plan view of the disposable pant in FIG. 9A.

In an modification of the disposable pant 15C, as shown in FIGS. 9A and 10A, a front stretchable multilayer member 17A defining an abdominal-side front zone P is formed with two cutting lines 18 each allowing the front stretchable multilayer member 17A to be manually cut in the width direction thereof. The front stretchable multilayer member 17A has a first end defining a waist opening T and a second end opposed to the first end, and each of the two cutting lines 18 is formed to extend between the first and second ends. Preferably, the two cutting lines 18 are formed parallel to one another to allow them to be simultaneously cut. Further, each of the cutting lines 18 is preferably formed to extend in a direction orthogonal to the first end defining the waist opening T so as to facilitate the cutting operation, and position-adjustment or alignment during an after-mentioned temporary engagement operation.

A hook element 11A of a mechanical fastener 11 is attached onto an inner surface of the front stretchable multilayer member 17A at a position located on each of outwardly right and left sides of the cutting lines 18, and a loop element 11B of the mechanical fastener 11 is attached onto an outer surface of one end (hereinafter referred to as "front end") 1a of the absorbent body 1 on the side of the abdominal-side front zone P.

Figure 9B:
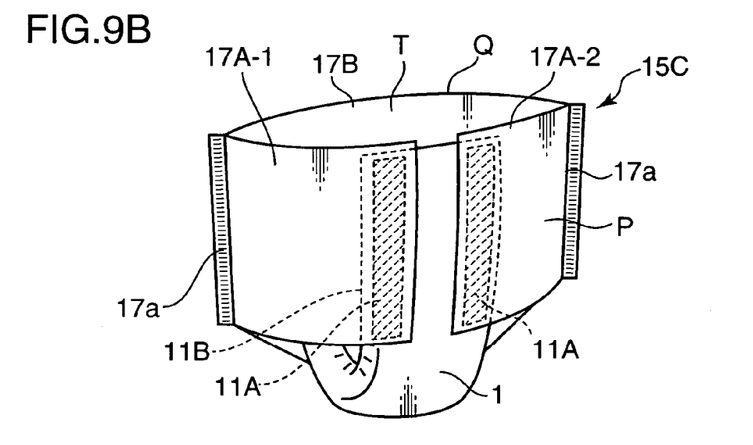
FIG. 9B is a perspective view thereof in the state after a portion between the two cutting line is removed.

Thus, after the front stretchable multilayer member 17A is cut along the cutting lines 18 in an urgent situation, and one or both of first and second cut segments 17A-1, 17A-2 of the front stretchable multilayer member 17A are opened rightwardly and/or leftwardly as with the disposable pant illustrated in FIG. 7B to allow a wearer to discharge his/her urine or the like in the state after the abdominal-side front zone P is opened, the cut segments 17A-1, 17A-2 can be temporarily engaged together by the mechanical fastener 11 to reconstruct a pant-like configuration and maintain it until the disposable pant 15C is changed to new one, as shown in FIG. 9B.

Figure 10B:
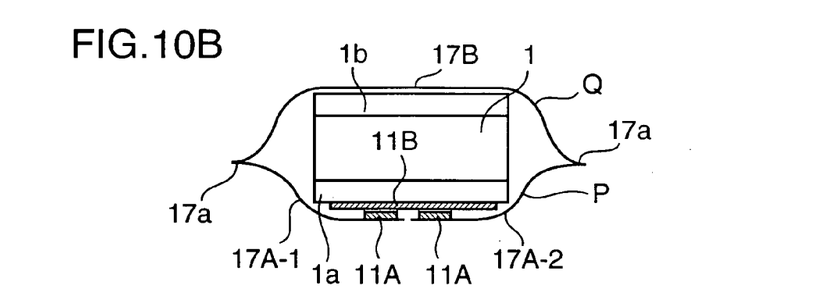
FIG. 10B is a top plan view of the disposable pant in FIG. 9B, wherein the first cut segment and a second cut segment are moved to get closer to one another.

In this case, after removing the area between the cutting lines 18, the first and second cut segments 17A-1, 17A-2 of the stretchable multilayer member 17A can be moved to get closer to one another and temporarily engaged to the absorbent body 1. This provides enhanced flexibility in an operation for adjusting the circumference of the abdominal-side front zone P.

Figure 9C:
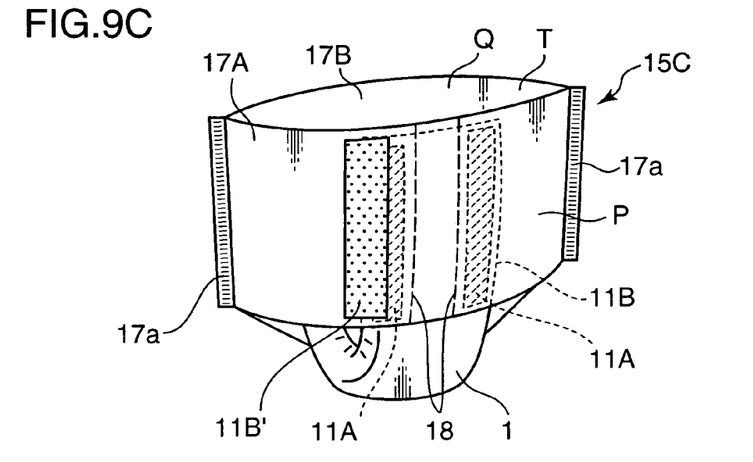
FIG. 9C is a perspective view thereof in the state after a loop element is attached to a first one of two cut segments.
Figure 10C:
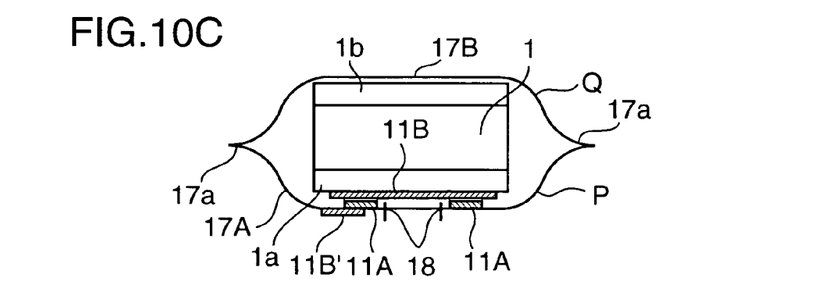
FIG. 10C is a top plan view of the disposable pant in FIG. 9A, wherein a loop element is attached thereto.

As shown in FIGS. 9C and 10C, an additional loop element 11B' of the mechanical fastener 11 may be attached onto the outer surface of an area having no cutting line 18 (aforementioned first cut segment 17A-1) in the front stretchable multilayer member 17A. If the outer surface of the front stretchable multilayer member 17A is made of a material detachably engageable with the hook element (e.g. air-through bonded nonwoven), it can be used as substitute for the loop element 11B'.

Figure 10D:
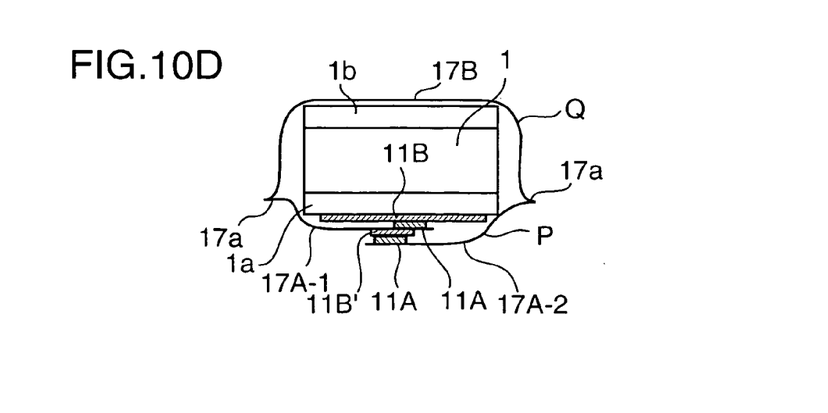
FIG. 10D is a top plan view of the disposable pant in FIG. 9C, wherein the second cut segment is partly superimposed on the first cut segment.

According to the above structure, as shown in FIG. 10D, the first cut segment 17A-1 of the front stretchable multilayer member 17A is disposed on the inside relative to the second cut segment 17A-2, and the hook element 11A of the first cut segment 17A-1 is engaged with the loop element 11B of the absorbent body 1. Then, the second cut segment 17A-2 is superimposed on the first cut segment 17A-1 from the outside to allow the hook element 11A of the second cut segment 17A-2 to be engaged with the loop element 11B' on the outer surface of the first cut segment 17A-1.

This provides enhanced flexibility in an operation for adjusting circumference of the abdominal-side front zone P.

In the third embodiment, the other end (hereinafter referred to as "rear end") 1b of the absorbent body 1 on the side of the dorsal-side rear zone Q is bonded to the rear stretchable multilayer member 17B defining the dorsal-side rear zone Q, and the cutting line 18 is formed in the front stretchable multilayer member 17A defining the abdominal-side front zone P. Further, the hook element 11A of the mechanical fastener 11 is attached to the front stretchable multilayer member 17A, and the loop element 11B of the mechanical fastener 11 is attached to the front end 1a of the absorbent body 1. Alternatively, the front end 1a of the absorbent body 1 may be bonded to the front stretchable multilayer member 17A, and the cutting line 18 may be formed in the rear stretchable multilayer member 17B. Further, the hook element 11A of the mechanical fastener 11 is attached to the rear stretchable multilayer member 17B, and the loop element 11B of the mechanical fastener 11 is attached to the rear end 1b of the absorbent body 1. Alternatively, the cutting line 18 may be formed in both the front and rear stretchable multilayer members, and the front and rear ends of the absorbent body 1 may be detachably engaged with the front and rear stretchable multilayer members, respectively.

Figure 11:
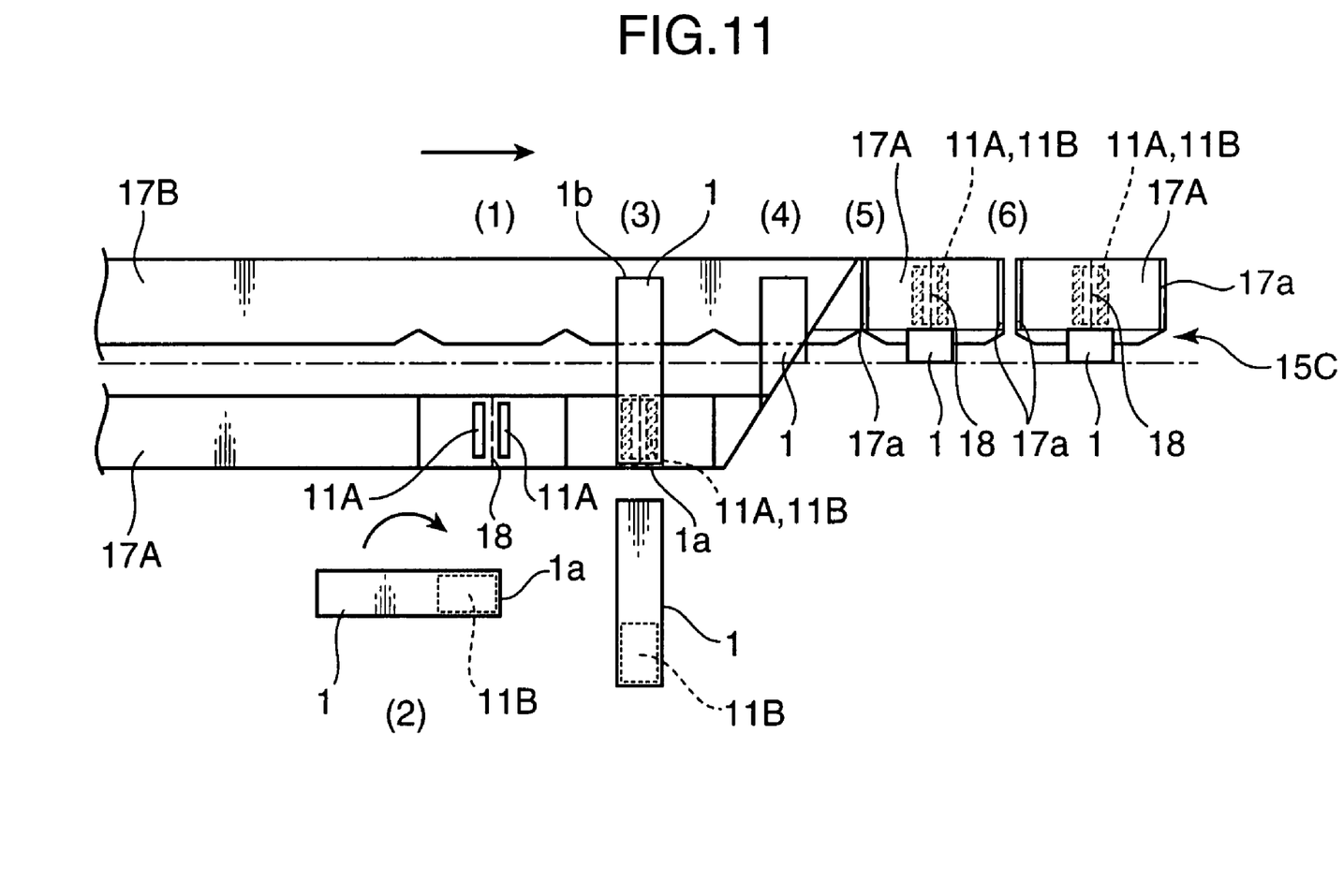
FIG. 11 is a production process diagram of the disposable pant according to the third embodiment.

FIG. 11 is a production process diagram of the disposable pant 15C according to the third embodiment.

A strip-shaped material of the front stretchable multilayer member 17A defining the abdominal-side front zone P and a strip-shaped material of the rear stretchable multilayer member 17B defining the dorsal-side rear zone Q are continuously fed in the longitudinal direction thereof while disposing them parallel to one another in the crosswise direction relative to the feed or machine direction with a given distance therebetween. During the feeding, the cutting line 18 is formed in the front stretchable multilayer member 17A, and the hook elements 11A of the mechanical fastener 11 are attached onto an upper surface (corresponding to the inner surface of the disposable pant 15C) of the front stretchable multilayer member 17A, at Step (1).

Then, at Step (2), the absorbent bodies 1 are produced while feeding them serially relative to the machine direction, and the loop element 11B of the mechanical fastener 11 is attached onto a back surface (corresponding to the outer surface of the disposable pant 15C) of the front end 1a of each of the absorbent bodies 1.

At Step 3, the absorbent body 1 is rotated at 90 degrees, and then the rear end of the absorbent body 1 is bonded to the rear stretchable multilayer member 17 B using hot melt adhesive or the like. Further, the loop element 11B on the front end 1a of the absorbent body 1 is engaged with the hook elements 11A of the front stretchable multilayer member 17A.

At Step 4, the front stretchable multilayer member 17A and the rear stretchable multilayer member 17B are superimposed on one another in such a manner that they be located on opposite sides of the absorbent body. At Step 5, respective portions of the front and rear stretchable multilayer members 17A, 17B to be formed as the lateral edges 17a are fusion-bonded together. Then, at Step 6, the obtained workpiece is cut along the side sealed portion to obtain finished individual disposable pants 15C, as shown in FIG. 7A. Preferably, the workpiece is cut between a pair of adjacent side-sealed portions at Step 6 to facilitate the cutting operation.

While the mechanical fastener is used as a fastening member in this specification, any other suitable fastening member, such as an adhesive tape, may be used in place of the mechanical fastener. The material or shape of the fastening member to be used for the disposable wearing article of the present invention is not limited to a specific type, but any suitable member or mechanism allowing detachable or peelable engagement may be used.

INDUSTRIAL APPLICABILITY

The disposable wearable article of the present invention has a side-sealed structure designed to fusion-bond the respective lateral edges of the abdominal-side front zone and the dorsal-side rear zone in a peelable manner so as to provide the side portions excellent in peel strength. Thus, in normal use, the side portions never get loose even if the disposable wearing article is used in a pant-like configuration for a long period of time.

Further, the structure designed to engage between the abdominal-side front zone and the dorsal-side rear zone by means of the fastening member is used in combination. Thus, after the side-sealed portion is peeled and separated in an urgent situation, the separated portions can be temporarily re-engaged using the fastening member to maintain a pant-like configuration until the wearing article is changed to new one.

This makes it possible to make full use of a costly disposable wearing article effectively.

What is claimed is:

1. A method of producing a disposable wearing article which includes a front stretchable multilayer member defining an abdominal-side front zone, a rear stretchable multilayer member defining a dorsal-side rear zone, an absorbent body disposed to bridge between said front stretchable multilayer member and said rear stretchable multilayer member, wherein said front stretchable multilayer member and said rear stretchable multilayer member are joined together to form a waist opening, said method comprising the steps of:
    continuously feeding said front stretchable multilayer member and said rear stretchable multilayer member with a given distance therebetween;
    preparing said absorbent body;
    forming at least one cutting line in said front stretchable multilayer member;
    attaching fastening members to an inner surface of said front stretchable multilayer member at both sides of said cutting line;
    bonding a rear end portion of said absorbent body to said rear stretchable multilayer member and detachably engaging a front end portion of said absorbent body with said fastening members attached to said front stretchable multilayer member so that the front end portion of said absorbent body is in opposed facing relationship to said cutting line; and
    superimposing said front stretchable multilayer member and said rear stretchable multilayer member in such a manner that they be located on opposite sides of said absorbent body, and joining respective portions of said superimposed stretchable multilayer members to be formed as lateral edges of said disposable wearing article.

2. The method as defined in claim 1, wherein said fastening member is adapted to allow said disposable wearing article in the state after said stretchable multilayer member formed with said cutting line is cut open to be reconstructed and used in a pant-like configuration.

3. The method as defined in claim 1, further comprising the step of:
    attaching a fastener detachably engageable with said fastening members attached to said front stretchable multilayer member at an outer surface of a front end portion of said absorbent body before the step of bonding the rear end portion of said absorbent body to said rear stretchable multilayer member.

4. The method as defined in claim 1, wherein the step of attaching fastening members to an inner surface of said front stretchable multilayer member at both sides of said cutting line includes attaching the fastening members at locations spaced from one another and spaced from the cutting line.

* * * * *